United States Patent
Segal (10) Patent No.: US 6,212,519 B1
(45) Date of Patent: Apr. 3, 2001

(54) SYSTEMS AND METHODS FOR QUANTIFYING QUALITATIVE MEDICAL EXPRESSIONS

(75) Inventor: Michael M. Segal, Brookline, MA (US)

(73) Assignee: SimulConsult, Inc., Brookline, MA (US)

( * ) Notice: Subject to any disclaimer, the term of this patent is extended or adjusted under 35 U.S.C. 154(b) by 0 days.

(21) Appl. No.: 09/107,885

(22) Filed: Jun. 30, 1998

(51) Int. Cl.[7] ....................................... G06F 17/30
(52) U.S. Cl. ...................... 707/6; 707/516; 705/2
(58) Field of Search ................... 707/6–7, 516; 705/2, 3

(56) References Cited

U.S. PATENT DOCUMENTS 4,667,292 * 5/1987 Mohlenbrock et al. ............... 705/2
6,026,363 * 2/2000 Shepard ................................ 705/3

FOREIGN PATENT DOCUMENTS 0 457000 A2 * 11/1991 (EP) ............................... 705/2

OTHER PUBLICATIONS

Gorry, G. and Barnett, G., "Experience with a Model of Sequential Diagnosis", *Computers and Biomedical Research*, 1:490–507 (1968).

* cited by examiner

Primary Examiner—Hosain T. Alam
Assistant Examiner—Jean Bolte Fleurantin
(74) Attorney, Agent, or Firm—Foley, Hoag, & Eliot LLP (57) ABSTRACT

The systems and methods of the invention can process a qualitative expression, typically a phrase, to generate a numerical value that represents the likelihood of an event as expressed by the given qualitative expression. The qualitative expressions typically are made up of a probability term and possibly a term of degree and one or more terms of negation. Thus, the systems described herein allow numerical information to be captured from qualitative expressions. This, allows further numeric processing and data refining, and facilitates the development of databases of information, such as databases of information about the significance of the existence of a symptom for the diagnosis of a particular disease.

16 Claims, 7 Drawing Sheets

| POSITIVE PROBABILITY | PROB(%) | NEGATION OF PROB (%) |
|---|---|---|
| possibly | 27 | 1 |
| sometimes | 33 | 2 |
| liable | 40 | 3 |
| prone | 40 | 3 |
| typically | 55 | 10 |
| frequently | 56 | 12 |
| often | 60 | 13 |
| likely | 63 | 14 |
| probably | 65 | 13 |
| commonly | 69 | 20 |
| generally | 70 | 20 |
| routinely | 70 | 20 |
| usually | 74 | 30 |
| regularly | 75 | 30 |
| ordinarily | 75 | 30 |
| normally | 79 | 40 |
| consistently | 80 | 40 |
| dependably | 80 | 40 |
| reliably | 80 | 40 |
| constantly | 90 | 65 |
| certainly | 95 | 70 |
| definitely | 95 | 80 |
| each | 95 | 80 |
| uniformly | 96 | 82 |
| totally | 98 | 86 |
| completely | 98 | 86 |
| all | 99 | 96 |
| always | 99 | 96 |
| every | 99 | 96 |
| VERY | Increases | probability |
| ALMOST | Decrease | probability |

Table 1A

| POSITIVE PROBABILITY | PROB(%) | NEGATION OF PROB (%) |
|---|---|---|
| never | 1 | 3 |
| rarely | 5 | 20 |
| sporadically | 5 | 20 |
| infrequently | 12 | 35 |
| seldom | 15 | 45 |
| low probability | 17 | 50 |
| doubtful | 20 | 60 |
| occasionally | 21 | |
| variably | 70 | 99 |
| doubtedly | 70 | 99 |
| VERY | Increases | probability |
| ALMOST | Decrease | probability |

Table 1B

Fig. 4

| POSITIVE DEGREE | FACTOR |
|---|---|
| quite | 0.3 |
| really | 0.5 |
| very | 0.6 |
| highly | 0.6 |
| entirely | 0.8 |
| exceedingly | 0.8 |
| absolutely | 0.9 |
| categorically | 0.9 |
|  |  |
|  |  |
|  |  |
|  |  |
|  |  |
|  |  |
| modify | reliably |

Table 2A

| NEGATIVE DEGREE | FACTOR |
|---|---|
| virtually | 0.05 |
| almost | 0.1 |
| nearly | 0.1 |
| relatively | 0.3 |
| fairly | 0.3 |
| somewhat | 0.5 |
| moderately | 0.5 |
| rather | 0.5 |
| pretty | 0.6 |
| slightly | 0.7 |
| hardly | 0.8 |
| barely | 0.9 |
| scarcely | 0.9 |
|  |  |
|  |  |
| modify | reliably |

Table 2B

Fig. 5

| OVERALL NEGATION | Degree | NEGATIVE PREFIX | PROBABILITY | PRESENCE | FORMULA FROM INITIAL PROB. | PROCESS FROM PREV. WORKING PROB |
|---|---|---|---|---|---|---|
| | | | pos | present | p | |
| | | | pos | absent | 1-p | |
| | | | neg | present | p | |
| | | | neg | absent | 1-p | |
| | | | | | | |
| | | neg | pos | present | p^4 | w^4 |
| | | neg | pos | absent | 1-(1-(1-p))^4 | 1-(1-w)^4 |
| | | neg | neg | present | 1-(1-p)^4 | 1-(1-w)^4 |
| | | neg | neg | absent | (1-p)^4 | w^4 |
| | | | | | | |
| | pos | | pos | present | p+f(1-p) | w+f(1-w) |
| | pos | | pos | absent | (1-p)(1-f) | w(1-f) |
| | pos | | neg | present | p(1-f) | w(1-f) |
| | pos | | neg | absent | (1-p)+fp | w+f(1-w) |
| | | | | | | |
| | neg | | pos | present | p(1-f) | w(1-f) |
| | neg | | pos | absent | (1-p)+fp | w+f(1-w) |
| | neg | | neg | present | p+f(1-p) | w+f(1-w) |
| | neg | | neg | absent | (1-p)(1-f) | w(1-f) |
| | | | | | | |
| | pos | neg | pos | present | p^4(1-f) | w(1-f) |
| | pos | neg | pos | absent | 1-p^4+fp^4 | w+f(1-w) |
| | | | | | | |
| neg | pos | | pos | present | (p+f(1-p))^4 | w^4 |
| neg | pos | | pos | absent | 1-(1-(1-p)(1-f))^4 | 1-(1-w)^4 |
| | | | | | | |
| | | neg | pos | present | p^4 | w^4 |
| neg | | | pos | present | p^4 | w^4 |
| | neg | | | | | |
| neg | neg | neg | pos | present | (p(1-f))^4 | w^4 |
| neg | pos | neg | pos | present | 1-(1-(p^4+f(1-p^4)))^4 | 1-(1-w)^4 |
| neg | neg | neg | pos | present | 1-(1-p^4(1-f))^4 | 1-(1-w)^4 |
| | | neg | pos | present | p^4+f(1-p^4) | w+f(1-w) |
| neg | | | pos | present | 1-(1-p^4)^4 | 1-(1-w)^4 |
| | neg | | | | | |
| | neg | | | absent | 1-p+f(1-(1-p)) | w+f(1-w) |
| neg | pos | | (frequently) | absent | 1-(p-fp)^4 | 1-(1-w)^4 |
| | pos | | (frequently) | present | p+f(1-p) | w+f(1-w) |
| neg | | | | present | (p+f(1-p))^4 | w^4 |
| | | | | | | |
| neg | | | | present | 1-present | |
| | | | | present | present | |
| neg | | | | absent | 1-present | |
| | | | | absent | present | |

Table 3

Fig. 6

Source code for Verbal Probability

```
final double getProbability()
{
        if (negationChoice.getSelectedIndex()!=0 && probChoice.getSelectedIndex() ==0)

return(-10); // error if modify a non-existent probability term
        if(probChoice.getSelectedIndex()==0)
        {
           probability=getChoiceValue (presenceSort);
           if(degreeChoice.getSelectedIndex()!=0)
           {
                if(positiveChoice(degreeSort))
                        probability=probability*probSort[6].value;//~frequently
                   probability=degreeModify( probability,
                        positiveChoice(presenceSort) == positiveChoice(degreeSort));
                if(notChoice.getSelectIndex()!=0) probability=negate ( probability,
                        positiveChoice(presenceSort)); //only this one is appropriate
           }
           else if (notChoice.getSelectedIndex() !=0) probability=1.0- probability;
}
else
{
           if(positiveChoice (presencesSort)) probability getChoiceValue(probSort);
           else probability = 1- getChoiceValue(probSort);
           if(negationChoice.getSelectedIndex() !=0) probability = negate ( probability,
                   positiveChoice(presenceSort) == positiveChoice(probSort));
           if (degreeChoice.getSelectedIndex() !=0) probability = degreeModify ( probability,
                   ((positiveChoice(presenceSort) == positiveChoice(probSort)) ==
                   positiveChoice(negationSort)) == positiveChoice(degreeSort));
           if (notChoice.getSelectedIndex() !=0) probability = negate ( probability,
                   (positiveChoice(presenceSort) == positiveChoice(probSort)) ==
                   positiveChoice(negationSort); //only these three are appropriate
    }
    return (probability);
} final double degreeModify (double p, boolean evenRelevantNegations)
{
        if(evenRelevantNegations) return (p+getChoiceValue(degreeSort)*(1.0-p));
        return (p* (1.0-getChoiceValue(degreeSort))):
} final double negate (double p, boolean evenRelevantNegations)
{
        if(evenRelevantNegations) return (p*p*p*p);
        double temp = 1.0-p;
        return (1.0-temp*temp*temp*temp);
}
```

Table 4

Fig. 7

SYSTEMS AND METHODS FOR QUANTIFYING QUALITATIVE MEDICAL EXPRESSIONS

FIELD OF THE INVENTION

The invention relates to systems and methods for creating databases of information, and more particularly, for creating databases of statistical data for applications such as diagnosing medical conditions.

BACKGROUND OF THE INVENTION

The process of diagnosing an illness or a disease typically involves recording the demographic information about the patient and documenting the findings that the patient is exhibiting. Together the demographic information and the finding information provide a patient profile. The diagnosing physician can compare the demographic information and the finding information of the patient against a listing of the common and descriptive findings for a particular disease, and can determine the likelihood that such a disease would be present in a patient having the information set forth in the profile.

For this process to work well, the physician must be provided with a database of information that sets forth the descriptive symptoms for a particular disease. Unfortunately, this information is difficult to come by. Frequently, the doctor must rely on personal experience, or search through the literature to identify studies that set forth statistical ranges indicating the likelihood that a particular finding is present in a patient with a particular disease. Often, however, the literature only offers general qualitative discussions as to the frequency or relevancy of a particular finding for a particular disease. Such qualitative expressions include statements that a particular disease is "very frequently" accompanied by a particular finding or that the finding is "almost never absent" in a patient with a particular disease. Similar qualitative expressions are used to describe the likelihood that a patient with a certain demographic profile will have a particular disease.

Although qualitative expressions provide information as to the probability that a particular finding will be seen in a patient suffering from a particular disease, the information is conveyed in a somewhat ambiguous manner and lacks the precision of a numerical statement that typically would be provided by a rigorous statistical analysis. However, patient studies that result in rigorous statistical analysis are few and far between. The scarcity of such publications arises in part from the difficulty in obtaining research support for analyzing a sufficiently large pool of candidates to come away with meaningful statistical data. Consequently, much of the diagnostic information available to a treating physician is in the form of qualitative expressions.

Accordingly, there is a need in the art for a system that can extract reliable and meaningful information from qualitative expressions.

SUMMARY OF THE INVENTION

It is an object of the invention to provide systems and methods that can evaluate qualitative expressions of likelihood to provide a more precise measure of statistical meaning.

The systems and methods of the invention can process a qualitative expression, typically a phrase to generate a numerical value that represents the likelihood of an event as expressed by the given qualitative expression. The qualitative expressions typically are made up of a probability term and possibly a term of degree and one or more terms of negation. Thus, the systems described herein allow numerical information to be captured from qualitative expressions. This, allows further numeric processing and data refining, and facilitates the development of databases of information, such as databases of information about the significance of the existence of a symptom for the diagnosis of a particular disease.

The systems described herein allow the use of qualitative information from separate sources to be combined in a meaningful way. For example, the systems described herein can average numbers that were obtained from the analysis of qualitative expressions from two different articles.

To this end, the systems described herein analyze a qualitative expression by examining each of the terms of that expression. The systems can identify those words which can be understood as probability terms and which can be associated with known numerical values of probability. For example, the qualitative expression may include the probability term "frequently", which may be known by the system to have, in certain contexts, an associated numerical probability value of about 56%. In one embodiment, the systems include a table of these known probability terms and the associated numerical probabilities. The system then analyzes the other terms in the expression, including terms of degree and terms of negation, and processes how these other terms impact on the numerical probability associated with the probability term. The resulting numerical value is understood to capture in a numerical format the probabilistic information provided by the qualitative expression.

In one embodiment, the invention provides processes for generating a numerical value of likelihood. These processes include the steps of identifying a qualitative expression of likelihood, having at least one term, parsing the qualitative expression as a function of the at least one term to identify a semantic form related to the qualitative expression, identifying for that one term a numerical value of probability associated with that one term, identifying, as a function of the semantic form, a formula for processing the numerical value of probability, and processing the numerical value of probability as a function of the formula to determine a numerical value of likelihood associated with the qualitative expression. In these processes qualitative expressions, such as the expression "most likely absent," can be identified from the medical literature and employing the processes of the invention, analyzed to generate a numerical value of probability associated with that qualitative expression. The qualitative expressions can include identifying terms that are representative of terms of degree, such as the term "very," and can identify whether the term is a positive or negative degree term. Similarly, when parsing the qualitative expression, the processes described herein can identify whether the qualitative expression includes terms of negation, such as the term "not."

In one process, identifying a numerical value of probability includes a step of searching a table for a numerical value of probability associated with the term, and identifying whether the term is a positive or negative probability term. In one process, identifying a formula as a function of a semantic form includes selecting a formula associated with the semantic form. In one practice, the form is selected from a table which includes a plurality of formulas wherein each formula is associated with at least one semantic form. In a further practice, the step of identifying a formula can include a step of generating a formula as a function of combining at least two related formulas. In further practice, the process includes a step of providing a table of weighting factors, wherein each factor is associated with a term of degree. Accordingly, each term of degree can have associated with it a numerical value that indicates quantitatively the effect of the term of degree on the qualitative expression.

The invention described herein can also include systems for generating a database of statistical data of medical information. These systems can include an input device for receiving a text string representative of a qualitative expression of the likelihood of the occurrence of an event, a parser for parsing the qualitative expression into one or more terms, including at least one term representative of a statement of likelihood, and for selecting a semantic form as a function of the parsed qualitative expression associated with the qualitative expression. These systems can also include a selection processor for selecting, for each term in a qualitative expression, a numerical value and a numerical processor for processing the selected numerical value as a function of the formula to provide a numerical value of likelihood associated with the qualitative expression. These systems can then include an updating processor that can update a database of numerical values. In one embodiment, these systems also include text filters that can sort through a body of text to identify therein qualitative expressions of likelihood that can be processed by the system described above.

BRIEF DESCRIPTION OF THE DRAWINGS

The foregoing and other objects and advantages of the invention will be appreciated more fully from the following further description thereof, with reference to the accompanying drawings wherein;

FIGS. 4 through 7 depict tables suitable for use with the systems described herein.

DETAILED DESCRIPTION OF THE ILLUSTRATED EMBODIMENTS

The invention will now be described with reference to a system that processes qualitative expressions to determine numerical values of probability. The system employs these numerical values of probability to build a database of probability data that can determine the likelihood that the presence or absence of a particular finding affects the likelihood of a patient having a particular disease or disorder. However, it will be understood that the invention can be employed for determining a numerical value from a qualitative expression for any suitable application, and is not to be limited to the embodiments described herein. Moreover, it will be understood that the systems of the invention are not to be limited to the hardware and software described herein, and that it will be understood by one of ordinary skill in the art that other hardware or software can be employed. For example, the invention can include an automatic front-end that will sort through text documents to identify qualitative expressions therein. These systems can automatically process qualitative expressions to determine a numerical value of probability. This numerical value of probability can be stored in the database generated by the system, or employed for any other suitable reason.

In one embodiment, the invention provides a system that processes qualitative expressions to determine numerical values of probability, and employs these numerical values of probability to build a database of probability data that represents the likelihood that the presence of a particular finding occurs in a particular disease or disorder.

Figure 1:
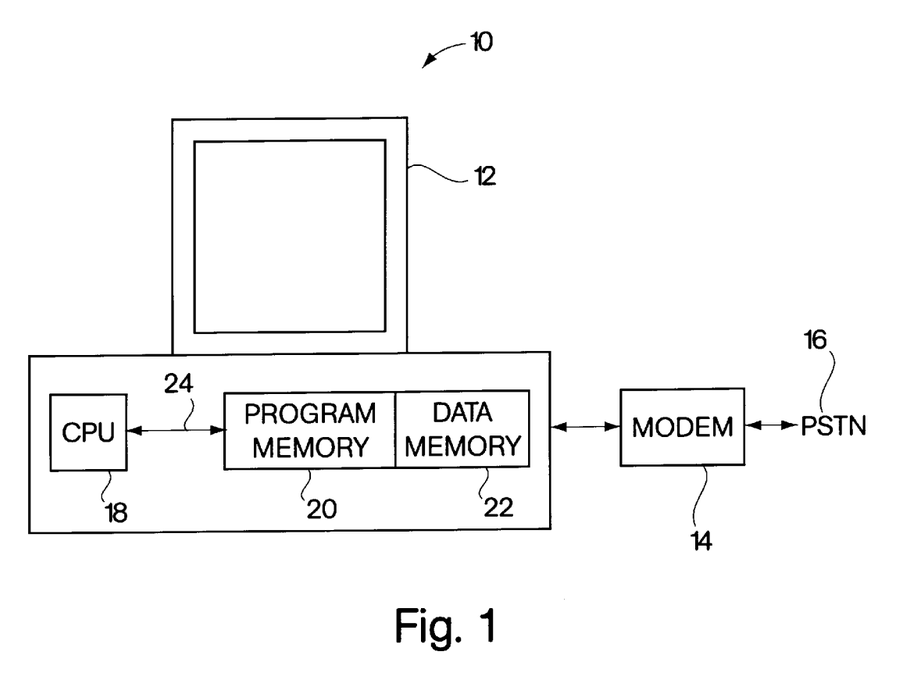
FIG. 1 depicts one system according to the invention.

In this embodiment, the system can be a computer program adapted to run on a conventional computer system, such as an IBM PC computer system. One such system is depicted in FIG. 1. Specifically, FIG. 1 depicts a system 10 that includes a conventional computer 12 which connects to a modem 14 which couples the computer 12 to the Public Switching Telephone Network (PSTN) 16. The computer 12 depicted in FIG. 1 includes a CPU 18, a program memory 20, a data memory 22, and a computer bus 24. The CPU 18 can be any conventional central processing unit, and typically will include an arithmetic logic unit, a set of internal registers, and a control unit. The program memory 20 can be a conventional volatile computer memory, such as a circuit card assembly providing random access memory (RAM) for use by the CPU. The data memory 22 can be a persistent memory device such as a hard disk, a floppy disk, or a tape drive. The bus 24 can be a conventional computer bus, such as the ISA bus, which carries data between the CPU 18 and the other elements of the computer system 12.

The computer program can be installed on the persistent memory of the computer 12 and can execute within the program memory 20 of computer 12 under the control of the CPU 18. In this way, the computer program adapts the conventional computer system 12 to act as a machine according to the invention for processing qualitative expressions to determine numerical values of probability.

In one embodiment, a computer program is written as a Java applet that runs within a browser program operating on the computer system 12. As will be understood by one of ordinary skill in the art, a Java applet allows for client side processing. Accordingly, the Java applet described herein can be downloaded from a server located at a remote station. Typically, the Java applet would be downloaded through modem 14 and the PSTN 16 from a Web server located at a remote location. Although the computer program described herein can be written in any high level, or low level language, it will be understood that the Java programming language provides a computer program capable of running on a multiplicity different platforms, including Windows platforms, MacIntosh platforms, UNIX platforms, LINUX platforms, and any other suitable platforms that can operate a Java enabled browser. Moreover, it will be understood by one of ordinary skill in the art that the Java programming language is understood to provide compact code, which reduces the download time required for downloading the Java program from the remote Web server.

In one embodiment, the Java program described herein provides a medical diagnostic program that aids a medical professional in the diagnosis of a particular disorder, such as a neurological disorder. The program includes an interface that guides the medical professional through a series of screens each displayed on the computer 10 depicted in FIG. 1. The displays direct the medical professional to identify those findings in a particular patient. Findings can include symptoms, patient histories, laboratory tests, environmental factors, the patient's demographic profile or any other information. The program can employ the findings to suggest one or several possible diseases on the basis of the entered finding profile. To this end, the computer program includes a data file that operates as a database of probability information regarding the likelihood that a particular finding is present in a particular disease or disorder. This data file can be developed, in part, from the analysis of qualitative expressions found within the medical literatures. To facilitate this, the Java program can include functionality for processing a qualitative expression to generate from that qualitative expression a numerical value of probability indicating the likelihood that a particular finding would be present in a patient suffering from a particular disease. In one practice, the Java program provides a user with a system for entering new statistical data into the data file. Accordingly, the Java program can distribute the responsibility of updating, or increasing, the data file across many trusted medical professionals of different sites. This facilitates the expansion of the data file, and therefore increases the likelihood that a proper diagnosis will be provided by the diagnostic program.

In one embodiment, the system includes, or is part of, a computer network, such as the Internet or a similar network, wherein a plurality of computer systems on the network can include a computer program according to the invention for generating numerical values of qualitative expressions representative of the significance of a particular finding for a particular disease or category of disease or medical condition. In the network embodiment, the operation of generating numerical statistical data is distributed across the plurality of users on the network. This allows the distributed building of the database, and provides a uniform method of generating and capturing data and data records for the database.

To facilitate the collection of such data, the computer program can lead the user through several steps, each of which cooperates with the others to process the qualitative expression and to determine therefrom a numerical value of probability. In one practice, the Java program provides a graphical user interface that leads the user through these steps, prompting the user to enter information through several interface screens. The program then processes the entered information to generate data for updating the database of diagnostic probability information.

Figure 2:
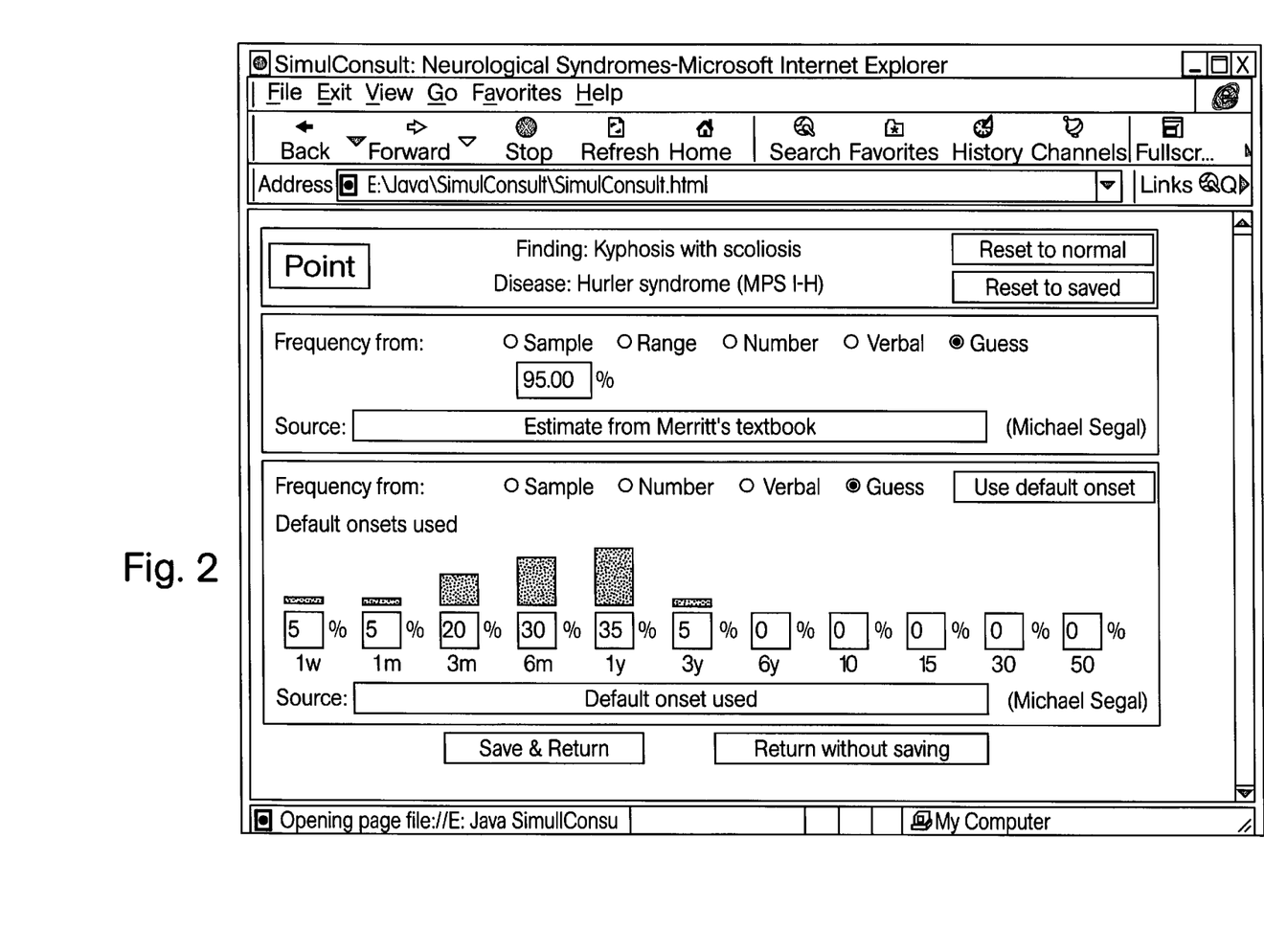
FIG. 2 depicts one user interface provided by a system of FIG. 1.

FIG. 2 shows an interface screen wherein the user is allowed to add information to the database. To this end, the interface screen prompts the user to enter a numerical value of probability, such as the 95% statistic depicted in FIG. 2. Accompanying the numerical value, the user is prompted to enter the source of the statistical information. For example, FIG. 2 illustrates that the user can select from the categories of: Sample, Range, Number, Verbal, or Guess. The Verbal selection indicates that the numeric value is generated by a verbal probability method wherein the system processes qualitative expressions found in the pertinent literature to determine a numerical value that is representative of the frequency or relevance of a finding with regard to a particular disease. Specifically, FIG. 2 depicts that the symptom Kyphosis without scoliosis is found in 95% of patients with Hurler Syndrome (MPS IH). FIG. 2 further depicts that the 95% numeric value is a guess, offered as an estimate taken from a reference source, such as Merritt's Textbook. Thus, the diagnostic database can store for a disease, a set of symptoms, each of which has an associated measure of frequency of occurrence. Moreover, for each such measure of frequency, the database can store information about the source of this measure. Although in the embodiment discussed the data collected has been representative of the frequency of a finding appearing in a patient, it will be understood that other measures of the relevance of a finding can be practiced with the invention without departing from the scope thereof.

Figure 3:
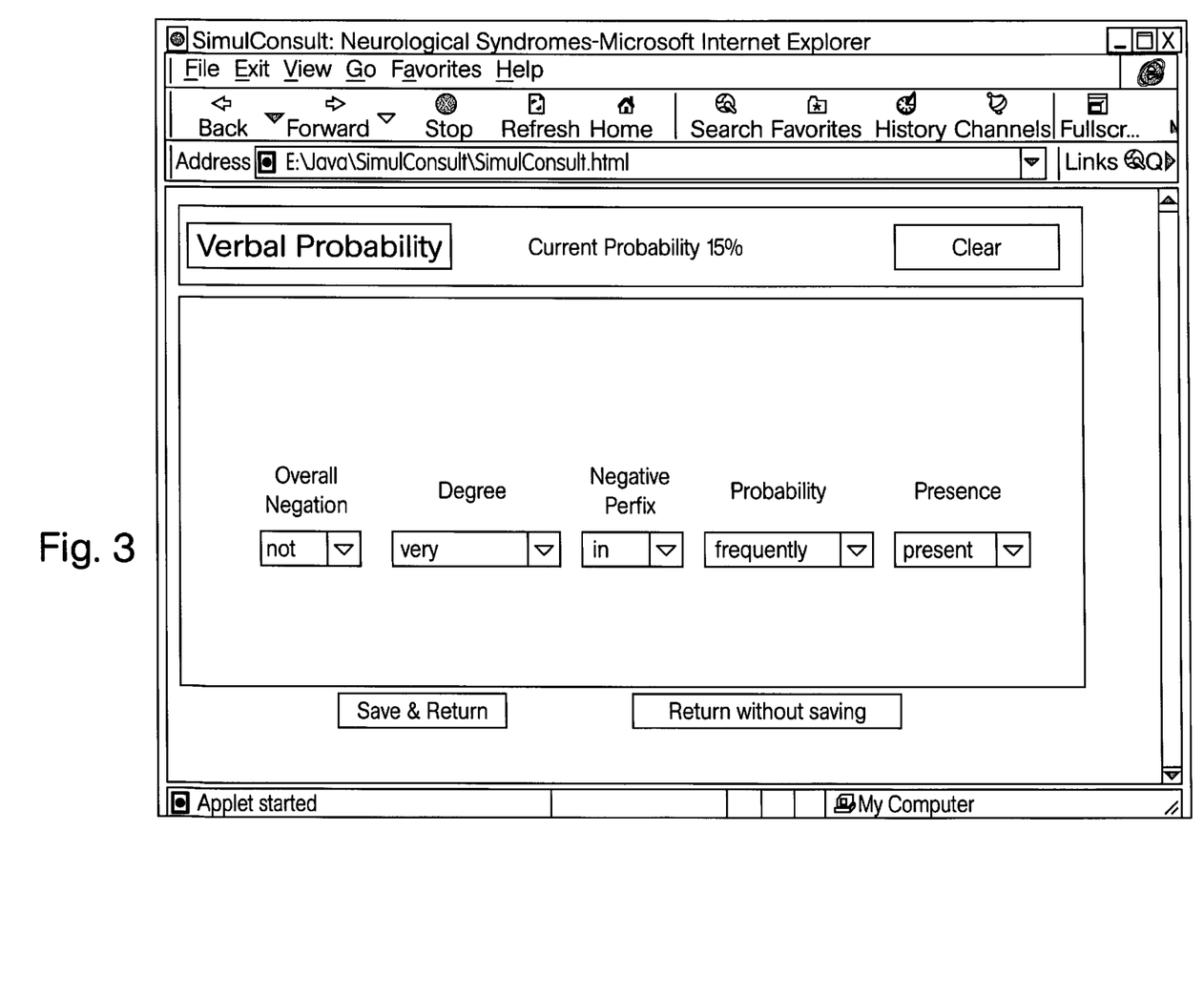
FIG. 3 depicts a user interface for directing the system of FIG. 1 to process a qualitative expression.

In FIG. 3, a screen that allows for generating a verbal probability is depicted. The user is allowed to enter, from left to right, a sequence of words that is semantically descriptive of the probability that a particular finding will be present in a patient afflicted with a particular disease. To that end, the screen of FIG. 3 allows a user to enter in the following information: whether the finding is present or absent, a probability term representative of the probability that the finding is present or absent, a negative prefix representative of whether the probability term is being employed affirmatively or negatively, a degree term representative of the degree with which the probability of the finding is present, and an overall negation term which represents whether the qualitative expression is an affirmative statement of likelihood or a negative statement of likelihood.

FIG. 3 further depicts that the current probability value is shown to the user. For example, FIG. 3 depicts that the current probability is measured at 15 percent. FIG. 3 further shows that the current probability of 15 percent is generated from a verbal probability analysis, as shown by the label "Verbal Probability."

The system analyzes the qualitative expression entered through the screen depicted in FIG. 3 to determine a numerical value representative of the probability that the finding will be identified within a patient having the particular disease. The system operates on the entered information, processing first the information on the right side of the screen. In a first step, the system determines the probability associated with the "presence" term. In subsequent steps, the system uses numerical values associated with the probability term and degree term employed in the expression. Numerical values can be obtained from the pertinent literature from surveys, or from any other suitable source.

Figure 4:
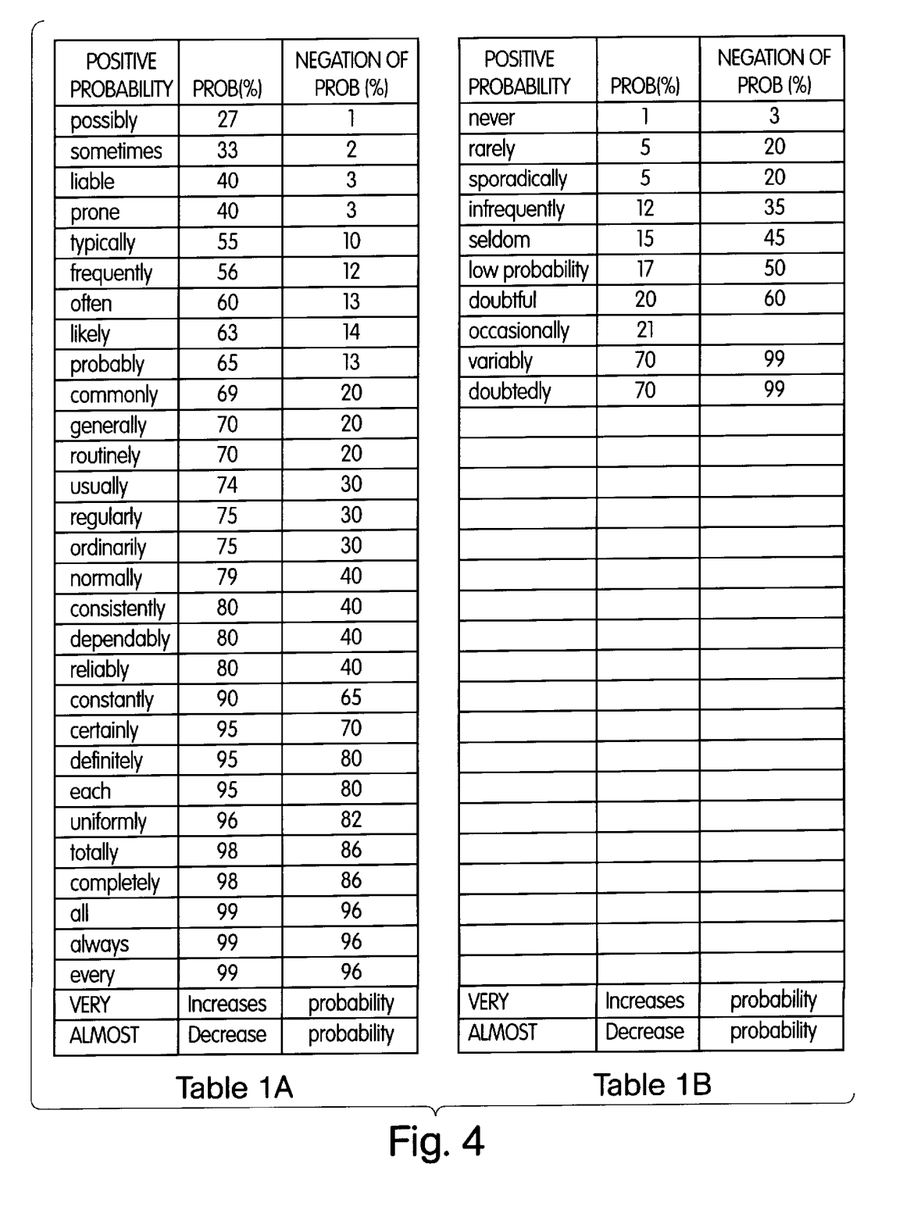

To this end, the system can store a set of tables providing a list of known probability terms, such as of the probability term "frequently" depicted in FIG. 3, along with a list of associated probabilities. In the embodiment depicted by FIG. 3, each of the listed probability terms can be offered in a selection box activated by the user, typically by clicking the down arrow on the box. Tables 1A and 1B illustrate tables of probability terms and associated probabilities.

Tables 1A and 1B depict examples of lists of terms that verbally indicate the probability that a symptom will be present or absent for a disease. The terms and their associated probabilities can be determined empirically, from analysis of medical literature, literature related to the study of qualitative expressions or by any other suitable technique.

The terms depicted by Table 1A are deemed to be positive probability terms. The positive probability terms depicted in Table 1A are understood as affirmative statements of the likelihood that a particular finding would be present or absent in a patient afflicted by particular disease or disorder. The numerical probability values of Table. 1A range from 27% to 99%, with 27% being the lowest probability and 99% being the highest. Conversely, Table 1B lists negative probability terms, which are understood to express affirmatively the improbability of a finding being present or absent in the same patient. The negative probability terms depicted in Table 1B range from a probability of 1% to a probability of 70%.

Table 1A has three columns. The first column lists the positive probability terms maintained by the Table, which in this embodiment represents the probability terms known to the system. The second column provides an empirical statement of probability given as a percentage value. The third column lists an empirical probability value associated with the term if that term is negated.

For example the 28th row of Table 1A states:

| | | |
|---|---|---|
| always | 99 | 96; |

Accordingly, the probability term "always" is considered as a positive probability term. In this example the probability term when applied to a finding that is present has a value of 99 percent. Accordingly, the numerical value associated with a statement that a particular symptom is "always" present is 99 percent. In the alternative, if the probability term "always" is negated, for example for the statement that a particular finding is "not always present" the associated numerical probability value, found from empirical studies, is 96 percent.

The mathematical relationship between a probability associated with a positive probability term and the probability associated with the negation of that same positive probability term can be represented by a quadratic function that can be fit to sets of data such as Table 1A. Specifically, a negation of a positive probability term having probability, p, can be modeled by the formula $p^4$. In general, the graphical presentation can include a graph having an x-axis representative of the positive probability associated with the term and the y-axis being representative of the negative probability associated. A graph can be made from a set of probability terms that have known values for both their positive and negative probability terms. From this graph, a function can be determined for translating between x values and y values, and perhaps between y values and x values. However, other techniques and other relationships can be determined and applied, and negated probabilities can be empirically or heuristically determined and stored in Table 1A.

Similarly, Table 1B provides a list of negative probability terms, and their associated probabilities and negated probabilities.

For example, row 2 states:

| | | |
|---|---|---|
| rarely | 5 | 20. |

Accordingly, Table 1B states that the probability associated with a statement a finding is "rarely present" is 5 percent. As discussed above, this numerical value associated with the probability term "rarely" can be determined from empirical studies, including studies from medical professionals. If the term "rarely" is negated, such as in the qualitative expression "not rarely present" the associated empirical probability is 20 percent.

The numerical value associated with a negative probability term can be determined by application of a formula, derived from an empirical analysis of data such as Table 1B, which is given by $1-(1-p)^4$.

Figure 5:
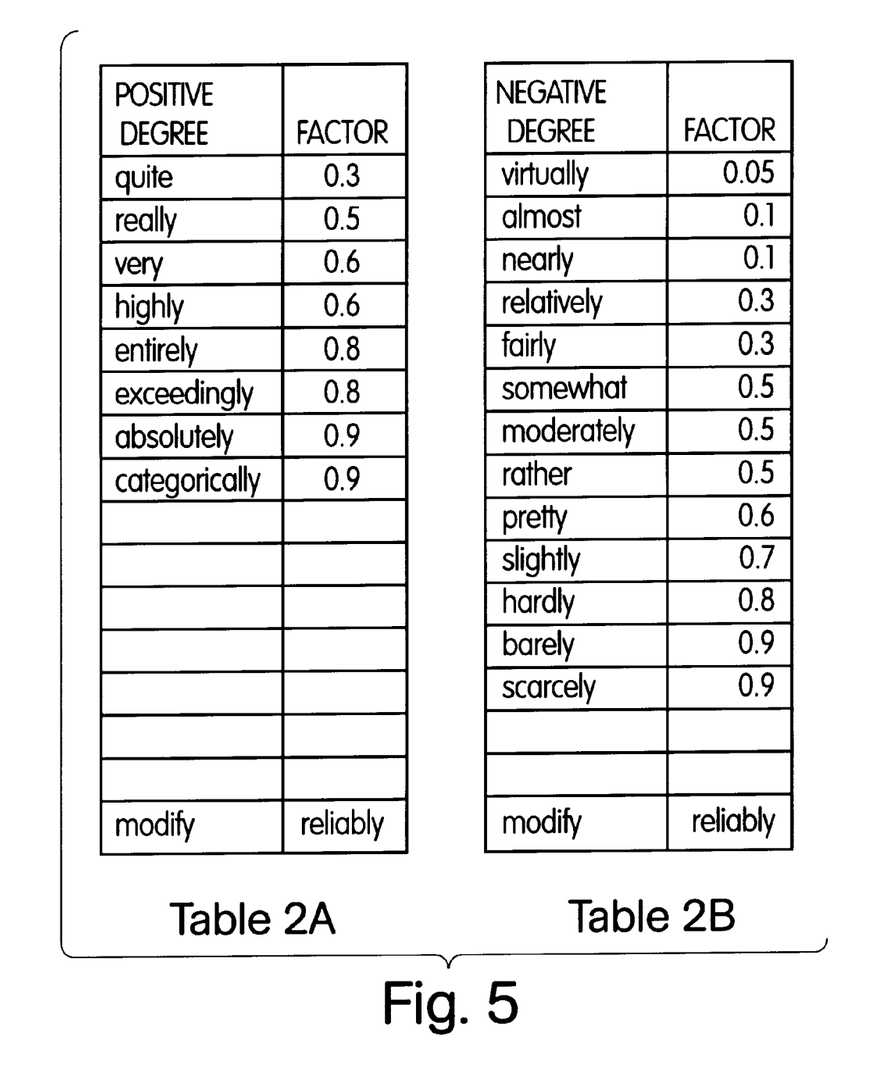

Similarly, Tables 2A and 2B provide two tables setting forth positive and negative statements of degree. Again, each of the positive and negative statements of degree can be selected from the selection box below the degree label depicted in FIG. 3. Each of the positive and negative adjectives is accompanied by a factor element which, in part, acts as a weighting element for increasing or decreasing the probability factor accompanying the respective qualitative expression selected from the probability selection box.

Once the user has selected the appropriate probability term indicating whether the finding is present or absent, selected the descriptive probability terms, and any associate negatives—the user can direct the program to generate a numerical value representative of the likelihood that the symptom is present.

In one practice, processes representing one or more negations, a probability term and a statement of degree are sequentially applied to generate a verbal probability value. Processes are applied depending on whether the probability terms are deemed by the system to be positive terms (Table 1A) or negative terms (Table 1B), and whether the degree terms are deemed by the system to be positive (Table 2A) or negative (Table 2B) degree terms.

Figure 6:
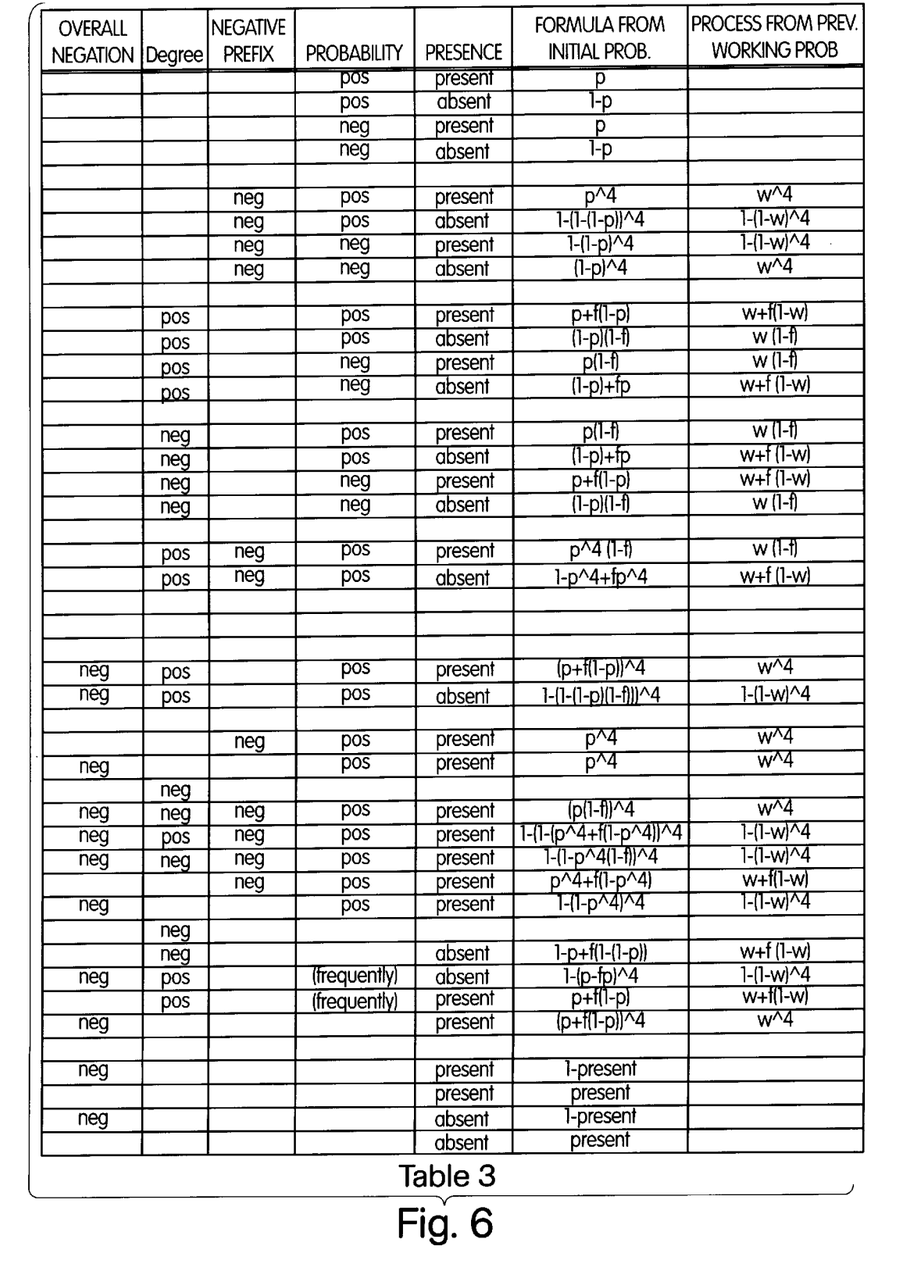

Table 3 provides examples of applying these processes to some of the many types of verbal probability expressions. In line 1 of the second grouping of examples, it can be seen that negation of a positive probability term for a finding being present is represented here by taking the $4^{th}$ power of the probability (i.e. $p^4$, as discussed earlier, entered in Table 3 in the column "Formula from initial probability"). In line 3 of the second grouping of examples, it can be seen that negation of a negative probability term for a finding being present is represented here by $1-(1-p)^4$, as discussed earlier.

Table 3 also illustrates handling of probability terms involving negative presence terms such as "absent". As indicated in lines 1 and 2 in the first grouping of examples, a positive probability term for a finding being present (e.g. "always present") is represented by the probability p, while a positive probability term for a finding being absent (e.g. "always absent") is represented by the probability 1–p, where p was the probability of the finding being present.

In this implementation, the formulae for negation of probability terms for findings being absent appear to be more complex (e.g. expressions such as $1-(1-(1-p))^4$ in line 2 of the second grouping for a verbal expression such as "not always absent"). However, when the operations are simplified to apply the verbal expressions from right to left, these seemingly complex equations can be reduced to a small number of mathematical processes operating on the working probability "w" generated from the result of processing the verbal terms to the right of the new term. As an example, the $1-(1-(1-p))^4$ term for "not always absent" can be expressed as $1-(1-w)^4$ when the previous result for the expression to the right of the "not" term (i.e. 1–p for "always absent") is represented as w. In this manner, it can be seen from Table 3 that the processes for negation of verbal probability reduce to two expressions: $w^4$ or $1-(1-w)^4$. The expression to be applied depends on the positive or negative nature of the presence term and probability term. In this representation, if the number of such negative terms is even, the $w^4$ process is applied, and if the number of such negative terms is odd, the $1-(1-w)^4$ process is applied. In this manner, negation can be applied as a simple process governed by the number of positive or negative terms in the verbal terms being parsed.

In a related way, degree terms can be divided into positive degree terms (FIG. 2A) and negative degree terms (FIG. 2B). Empirical weighting factors can be applied to represent the strength of the assertions made as "f" factors (Tables 2A and 2B). As is shown in Table 3, use of these degree terms was applied as processes operating on the working probability result "w" from terms to the right as a working probability "w". These two processes are w+f(1–w) and w(1–f). As can be seen from sections 3 and 4 of Table 3, these two processes account for all eight formulae in these sections, depending on whether there is an odd or even number of negative/absent terms. In this manner, degree terms are applied as a process governed by the positivity or negativity of the statement being made.

As is shown from subsequent sections in Table 3, negation of degree terms as well as double negation expressions can all be represented by these same pairs of negation processes and degree processes. See the column "Process from Previous Working Probability." In all cases, the choice of which negation or degree process to apply is determined by the number of positive or negative terms in the expressions being parsed.

For those situations in which no probability term is used, it is judged from empirical studies that the degree terms and negations of degree terms have an implied (though omitted) probability term of "frequently" for present findings (e.g. "very present" is taken as if it were "very frequently present").

This is the process of analysis of verbal probability terms, proceeding from right to left through the semantic order shown in FIG. 3, that is represented in the computer code provided. As is evident from the code, the two pairs of processes for negation and degree are applied to the empirical probability values in the middle columns of Tables 1A & 1B, and of the right columns of Tables 2A & 2B.

In one embodiment, the systems described herein for generating numerical measures of likelihood are employed with systems for supplementing or updating databases of information. In such systems, the verbal probability computed by the systems described herein can replace the existing probability or probabilities associated with the particular symptom and stored in the database. Thus, in one embodiment the old probability value is replaced with the newly calculated probability value. However, in alternative embodiments the measure of probability determined from the verbal probability analysis can be employed to adjust the stored probability value. For example, the measure determined from the verbal probability analysis can be averaged with the existing probability value and the averaged value can replace the existing stored value. Alternatively, a weighted average can be generated by the system. For example, the probability determined by the verbal probability process can be weighted by a value that reflects the process employed for generating the probability measure. For example, a probability measure determined from a rigorous statistical analysis can be given greater weight in the final averaged value than a probability measure determined from a verbal probability analysis or from a guess. It will be apparent to one of ordinary skill in the art that other techniques can be employed for determining a new measure of probability, and any such technique suitable for refining a probability measure can be employed without departing from the scope of the invention.

Those skilled in the art will know or be able to ascertain using no more than routine experimentation, many equivalents to the embodiments and practices described herein. For example, the systems described herein can be software systems operating on general purpose computer platforms, as well as hardware systems custom built or modified for functioning as the systems described herein.

Accordingly, it will be understood that the invention is not to be limited to the embodiments disclosed herein, but is to be understood from the following claims, which are to be interpreted as broadly as allowed under the law.

TABLE 1A

| POSITIVE PROBABILITY | PROB (%) | NEGATION OF PROB (%) |
|---|---|---|
| possibly | 27 | 1 |
| sometimes | 33 | 2 |
| liable | 40 | 3 |

TABLE 1A-continued

| POSITIVE PROBABILITY | PROB (%) | NEGATION OF PROB (%) |
|---|---|---|
| prone | 40 | 3 |
| typically | 55 | 10 |
| frequently | 56 | 12 |
| often | 60 | 13 |
| likely | 63 | 14 |
| probably | 65 | 13 |
| commonly | 69 | 20 |
| generally | 70 | 20 |
| routinely | 70 | 20 |
| usually | 74 | 30 |
| regularly | 75 | 30 |
| ordinarily | 75 | 30 |
| normally | 79 | 40 |
| consistently | 80 | 40 |
| dependably | 80 | 40 |
| reliably | 80 | 40 |
| constantly | 90 | 65 |
| certainly | 95 | 70 |
| definitely | 95 | 80 |
| each | 95 | 80 |
| uniformly | 96 | 82 |
| totally | 98 | 86 |
| completely | 98 | 86 |
| all | 99 | 96 |
| always | 99 | 96 |
| every | 99 | 96 |
| VERY | Increases | probability |
| ALMOST | Decrease | probability |

TABLE 1B

| NEGATIVE PROBABILITY | PROB (%) | NEGATION OF PROB (%) |
|---|---|---|
| never | 1 | 3 |
| rarely | 5 | 20 |
| sporadically | 5 | 20 |
| infrequently | 12 | 35 |
| seldom | 15 | 45 |
| low probability | 17 | 50 |
| doubtful | 20 | 60 |
| occasionally | 21 | |
| variably | 70 | 99 |
| doubtedly | 70 | 99 |
| VERY | Decreases | probability |
| ALMOST | Increases | probability |

TABLE 2A

| POSITIVE DEGREE | FACTOR |
|---|---|
| quite | 0.3 |
| really | 0.5 |
| very | 0.6 |
| highly | 0.6 |
| entirely | 0.8 |
| exceedingly | 0.8 |
| absolutely | 0.9 |
| categorically | 0.9 |
| modify | reliably |

TABLE 2B

| NEGATIVE DEGREE | FACTOR |
|---|---|
| virtually | 0.05 |
| almost | 0.1 |
| nearly | 0.1 |
| relatively | 0.3 |
| fairly | 0.3 |
| somewhat | 0.5 |
| moderately | 0.5 |
| rather | 0.5 |

TABLE 2B-continued

| NEGATIVE DEGREE | FACTOR |
|---|---|
| pretty | 0.6 |
| slightly | 0.7 |
| hardly | 0.8 |
| barely | 0.9 |
| scarcely | 0.9 |
| modify | reliably |

TABLE 3

| OVERALL NEGATION | DEGREE | NEGATIVE PREFIX | PROBA-BILITY | PRESENCE | FORMULA FROM INITIAL PROB. | PROCESS FROM PREV. WORKING PROB |
|---|---|---|---|---|---|---|
|  |  |  | pos | present | p |  |
|  |  |  | pos | absent | 1 − p |  |
|  |  |  | neg | present | p |  |
|  |  |  | neg | absent | 1 − p |  |
|  |  | neg | pos | present | p4 | w4 |
|  |  | neg | pos | absent | 1 − (1 − (1 − p))4 | 1 − (1 − w)4 |
|  |  | neg | neg | present | 1 − (1 − p)4 | 1 − (1 − w)4 |
|  |  | neg | neg | absent | (1 − p)4 | w4 |
|  | pos |  | pos | present | p + f (1 − p) | w + f (1 − w) |
|  | pos |  | pos | absent | (1 − p) (1 − f) | w (1 − f) |
|  | pos |  | neg | present | p(1 − f) | w (1 − f) |
|  | pos |  | neg | absent | (1 − p) + fp | w + f (1 − w) |
|  | neg |  | pos | present | p(1 − f) | w (1 − f) |
|  | neg |  | pos | absent | (1 − p) + fp | w + f (1 − w) |
|  | neg |  | neg | present | p + f (1 − p) | w + f (1 − w) |
|  | neg |  | neg | absent | (1 − p) (1 − f) | w (1 − f) |
|  | pos | neg | pos | present | p4 (1-f) | w (1 − f) |
|  | pos | neg | pos | absent | 1 − p4 + fp4 | w + f (1 − w) |
| neg | pos |  | pos | present | (p + f (1 − p))4 | w4 |
| neg | pos |  | pos | absent | 1 − (1 − (1 − p)(1 − f))4 | 1 − (1 − w)4 |
|  |  | neg | pos | present | p4 | w4 |
| neg |  |  | pos | present | p4 | w4 |
| neg | neg |  | pos | present | (p(1 − f))4 | w4 |
| neg | neg | neg | pos | present | 1 − (1 − (p4 + f(1 − p4))4 | 1 − (1 − w)4 |
| neg | pos | neg | pos | present | 1 − (1 − p4(1 − f))4 | 1 − (1 − w)4 |
|  |  | neg | neg | pos | present | p4 + f (1 − p4) | w + f (1 − w) |
| neg |  | neg | pos | present | 1 − (1 − p4)4 | 1 − (1 − w)4 |
|  | neg |  |  | absent | 1 − p + f (1 − (1 − p)) | w + f (1 − w) |
| neg | neg |  |  | absent | 1 − (p − fp)4 | 1 − (1 − w)4 |
|  | pos |  | (frequently) | present | p + f (1 − p) | w + f (1 − w) |
| neg | pos |  | (frequently) | present | (p + f (1 − p))4 | w4 |
| neg |  |  |  | present | 1 − present |  |
|  |  |  |  | present | present |  |
| neg |  |  |  | absent | 1 − present |  |
|  |  |  |  | absent | present |  |

Source code for Verbal Probability
final double getProbability()

```
{
    if (negationChoice.getSelectedIndex() != 0 && probChoice.getSelectedIndex() == 0)
        return (−1.0); // error if modify a non-existent probability term
    if (probChoice.getSelectedIndex() == 0)
    {
        probability = getChoiceValue (presenceSort);
        if (degreeChoice.getSelectedIndex() != 0)
        {
            if (positiveChoice(degreeSort))
                probability = probability * probSort[6].value; // ~frequently
            probability = degreeModify (probability,
                positiveChoice(presenceSort) == positiveChoice(degreeSort));
```

-continued

```
            if (notChoice.getSelectedIndex() != 0) probability = negate (probability,
                positiveChoice(presenceSort)); // only this one is appropriate
        }
        else if (notChoice.getSelectedIndex() != 0) probability = 1.0 - probability;
    }
    else
    {
        if (positiveChoice (presenceSort)) probability = getChoiceValue(probSort);
        else probability = 1- getChoiceValue(probSort);
        if (negationChoice.getSelectedIndex() != 0) probability = negate (probability,
            positiveChoice(presenceSort) == positiveChoice(probSort));
        if (degreeChoice.getSelectedIndex() != 0) probability = degreeModify (probability,
            ((positiveChoice(presenceSort) == positiveChoice(probSort))==
            positiveChoice(negationSort)) == positiveChoice(degreeSort));
        if (notChoice.getSelectedIndex() != 0) probability = negate (probability,
            (positiveChoice(presenceSort) == positiveChoice(probSort)) ==
            positiveChoice(negationSort)); // only these three are appropriate
    }
    return (probability);
}
final double degreeModify (double p, boolean evenRelevantNegations)
{
    if (evenRelevantNegations) return (p + getChoiceValue(degreeSort) * (1.0 - p));
    return (p * (1.0 - getChoiceValue(degreeSort)));
}
final double negate (double p, boolean evenRelevantNegations)
{
    if (evenRelevantNegations) return (p*p*p*p);
    double temp = 1.0 - p;
    return (1.0 - temp*temp*temp*temp);
}
```

I claim:

1. A process for generating a numerical value of likelihood of a symptom being present for a particular disease, comprising identifying a qualitative expression of likelihood having at least one term, parsing said qualitative expression as a function of said at least one term to identify a semantic form related to said qualitative expression, identifying for said at least one term a numerical value of probability associated with said at least one term, identifying, as a function of said semantic form, a formula for processing said numerical value of probability, and processing said numerical value of probability as a function of said formula to determine a numerical value of likelihood associated with said qualitative expression and providing a numerical statement of the likelihood that a particular symptom is present in a patient having a particular disease.

2. A process according to claim 1, wherein parsing said qualitative expression includes identifying terms representative of terms of degree, and identifying whether the term is a positive or negative degree term.

3. A process according to claim 1, wherein parsing said qualitative expression includes identifying terms representative of terms of negation.

4. A process according to claim 1, wherein identifying a numerical value of probability includes searching a table for a numerical value of probability associated with said term and identifying whether the term is a positive or negative probability term.

5. A process according to claim 1, wherein identifying a formula as a function of semantic form includes choosing a formula associated with said semantic form.

6. A process according to claim 1, wherein identifying a formula includes generating a formula as a function of combining at least two related formulas.

7. A process according to claim 6, wherein combining said at least two related formula includes combining said at least two related formula as a function of whether the qualitative expression is an affirmative or negative expression of likelihood of an event occurring, and whether the probability of degree terms are deemed positive or negative terms.

8. A process according to claim 1, including providing a table of weighting factors, each of which is associated with a term of degree.

9. A process according to claim 1, including applying weighting terms to a qualitative expression as a function of whether the qualitative expression is an affirmative or negative expression of likelihood of an event occurring.

10. A process for generating a numerical value of the likelihood of a symptom being present for a particular disease, comprising identifying a qualitative expression of a likelihood that a particular symptom is present in a patient having a particular medical condition, wherein said qualitative expression includes a term for expressing likelihood, parsing said qualitative expression as a function of said term to identify a semantic form related to said qualitative expression, identifying for said term a numerical value of probability associated with said term, identifying, as a function of said semantic form, a formula for processing said numerical value of probability, and processing said numerical value of probability as a function of said formula to determine a numerical value of likelihood associated with said qualitative expression and providing a numerical statement of the likelihood that a particular symptom is present in a patient having a particular disease.

11. A system for generating a database of statistical data of medical information, comprising
   an input device for receiving a text string representative of a qualitative expression of the likelihood of the occurrence of an event, a parser for parsing said qualitative expression into one or more terms, including at least one term representative of a statement of likelihood, and for selecting a semantic form, as a function of said parsed qualitative expression, associated with said qualitative expression,
   a selection processor for selecting for each term in said qualitative expression a numerical value, and
   a numerical processor for processing said selected numerical values as a function of said formula, to provide a numerical value of likelihood associated with said qualitative expression and providing a numerical statement of the likelihood that a particular symptom is present in a patient having a particular disease.

12. A system according to claim 11, further comprising means for updating a database of numerical values.

13. A system according to claim 12, further comprising means for adding a record including said generated numerical value of likelihood into a database.

14. A system according to claim 12, including means for averaging said generated numerical value with a numerical value store said database.

15. A system according to claim 14, further including means for generating weighed averages of numerical values.

16. A system according to claim 11, further including a text processor for identifying within a body of text a qualitative expression of likelihood.

* * * * *